(12) United States Patent
Cook et al.

(10) Patent No.: US 8,372,654 B2
(45) Date of Patent: Feb. 12, 2013

(54) METHOD FOR INVESTIGATING THE FATE OF A TEST COMPOUND OR THE STATE OF A BIOLOGICAL SYSTEM BY MEANS OF NMR OF HYPERPOLARISED NMR ACTIVE NUCLEI

(75) Inventors: Neil Cook, Dover, MA (US); Albie Santos, Cardiff (GB); Nigel Bosworth, Cardiff (GB); Jan Wolber, Cardiff (GB); Mike Looker, Cardiff (GB); Peter Knox, Wokingham (GB); Jan Jenrik Ardenkjaer-Larsen, Malmo (SE); Klaes Golman, Malmo (SE)

(73) Assignee: GE Healthcare Limited, Buckinghamshire (GB)

( * ) Notice: Subject to any disclaimer, the term of this patent is extended or adjusted under 35 U.S.C. 154(b) by 1371 days.

(21) Appl. No.: 10/311,108

(22) PCT Filed: Jun. 12, 2001

(86) PCT No.: PCT/GB01/02559
§ 371 (c)(1),
(2), (4) Date: Jul. 17, 2003

(87) PCT Pub. No.: WO01/96895
PCT Pub. Date: Dec. 20, 2001

(65) Prior Publication Data
US 2004/0039281 A1   Feb. 26, 2004

(51) Int. Cl.
*G01N 1/00* (2006.01)
(52) U.S. Cl. ........ 436/174; 600/410; 324/307; 324/309; 436/173; 424/9.3
(58) Field of Classification Search .................. 600/420, 600/410, 407; 424/93, 178.1; 324/307–309, 324/312, 318; 435/7.1; 514/12; 436/173, 436/174
See application file for complete search history.

(56) References Cited

U.S. PATENT DOCUMENTS 5,433,196 A * 7/1995 Fiat .............................. 600/410
5,642,625 A * 7/1997 Cates et al. .................... 62/55.5
(Continued)

FOREIGN PATENT DOCUMENTS

WO   WO97/37239   10/1997
WO   WO98/58272   12/1998
(Continued)

OTHER PUBLICATIONS

RR Rizi. A New Direction for Polarized Carbon-13 MRI. Proceedings of the National Academy of Sciences. 2009; 106(14): 5453-5454.*

(Continued)

*Primary Examiner* — Brian Casler
*Assistant Examiner* — Amanda Lauritzen
(74) *Attorney, Agent, or Firm* — Jean K. Testa

(57) ABSTRACT

The invention is concerned with Nuclear Magnetic Resonance (NMR) spectroscopy and Magnetic Resonance Imaging (MRI), particularly NMR spectroscopy. It provides hyperpolarization methods offering enhanced sensitivity of detection over conventional NMR for studying the fate of a test compound in a biological system. The methods are particularly suitable for studying metabolism and toxicity of drugs. The resulting NMR sensitivity increase is advantageous in two key aspects of NMR detection: test compounds can be detected at lower concentrations and substantial time saving can be achieved in cases where extensive averaging is conventionally employed to increase the signal to noise ratio of the corresponding NMR spectra. The methods can be used for studios that were not practical or not possible using conventional NMR.

5 Claims, 3 Drawing Sheets

U.S. PATENT DOCUMENTS

| | | | |
|---|---|---|---|
| 5,789,921 A * | 8/1998 | Albert et al. | 324/300 |
| 6,426,058 B1 * | 7/2002 | Pines et al. | 424/9.3 |
| 6,566,875 B1 * | 5/2003 | Hasson et al. | 324/309 |
| 6,666,047 B1 * | 12/2003 | Shah et al. | 62/637 |
| 6,845,262 B2 * | 1/2005 | Albert et al. | 600/420 |
| 2001/0037063 A1 * | 11/2001 | Albert et al. | 600/420 |
| 2005/0030026 A1 * | 2/2005 | Pines et al. | 324/309 |
| 2006/0171891 A1 * | 8/2006 | Ardenkjaer-Larsen et al. | 424/9.3 |
| 2007/0265520 A1 * | 11/2007 | Posse | 600/410 |
| 2008/0061781 A1 * | 3/2008 | Servin et al. | 324/311 |
| 2008/0095713 A1 * | 4/2008 | Thaning et al. | 424/9.3 |
| 2008/0116890 A1 * | 5/2008 | Hurd | 324/311 |

FOREIGN PATENT DOCUMENTS

| | | |
|---|---|---|
| WO | WO 98/58272 | * 12/1998 |
| WO | WO00/40988 | 7/2000 |

OTHER PUBLICATIONS

S Hu, AP Chen, ML Zierhut, R Bok, Y-F Yen, MA Schroeder, RE Hurd, SJ Nelson, J Kurhanewicz, DB Vigneron. In Vivo Carbon-13 Dynamic MRS and MRSI of Normal and Fasted Rat Liver with Hyperpolarized 13C-Pyruvate. Molec Imag and Biol. 2009; 11: 399-407.*

PA Bottomley, CJ Hardy, PB Roemer, OM Mueller. Proton-Decoupled, Overhauser-Enhanced, Spatially Localized Carbon-13 Spectroscopy in Humans. Magn Resn in Med. 1989; 12: 348-363.*

Wolber, J., et al. "In Vitro and In Vivo NMR and MRI with Optically Polarised Xenon in Solution" Extended Abstracts of the Joint 29th AMPERE—13th ISMAR International Conference, "Magnetic Resonance and Related Phenomena" vol. 1, Aug. 2, 1998.

Wolber, J., et al. "Hyperpolarized 129Xe NMR as a Probe for Blood Oxygenation" Magnetic Resonance in Medicine, Academic Press, Duluth, MN, US vol. 43, No. 4, Apr. 2000 pp. 491-496.

Gillies, R. J., Ed.: "NMR in Physiology and Biomedicine" 1994, Academic Press Inc., London chapter 14, p. 221-236, Bell, J. D., et al. "NMR Studies of Body Fluids and Tissue Extracts".

Hall, D. A., et al. "Polarization-Enhanced NMR Spectroscopy of Biomolecules in Frozen Solution" Science, American Association for the Advancement of Science, US vol. 276, No. 5314, May 9, 1997 pp. 930-932.

Foster, M. A., et al. "The application of PEDRI to the study of free radicals in vivo" Physics in Medicine and Biology, Jul. 1998, IOP Publishing, UK vol. 43, No. 7 pp. 1893-1897.

Nicholson, J., et al. "'Metabonomics': Understanding the metabolic responses of living systems to pathophysiological analysis of biological NMR spectroscopic data" Xenobiotica vol. 29, No. 11, Nov. 1999 pp. 1181-1189.

Paul A. Bottomley, et al, Proton-Decoupled, Overhauser-Enhanced, Spatially Localized Carbon-13 Spectroscopy in Humans, Magnetic Resonance in Medicine 12, pp. 348-363, 1989.

Simon Hu, et al, "In Vivo Carbon-13 Dynamic MRS and MRSI of Normal and Fasted Rat Liver With Hyperpolarized 13C-Pyruvate", Mol Imaging Biol (2009) 11:399-407.

Rahim R. Rizi, "A New Direction for Polarized Carbon-13 MRI", PNAS, vol. 106, No. 14, pp. 5453-5454, Apr. 7, 2009.

* cited by examiner

METHOD FOR INVESTIGATING THE FATE OF A TEST COMPOUND OR THE STATEOF A BIOLOGICAL SYSTEM BY MEANS OF NMR OF HYPERPOLARISED NMR ACTIVE NUCLEI

Technical Field

This invention is concerned with Nuclear Magnetic Resonance (NMR) spectroscopy and Magnetic Resonance Imaging, particularly NMR spectroscopy. The spectra of NMR active nuclei vary depending on their environment. The present invention provides a method for obtaining information regarding the fate of a test compound, which may be exogenous, e.g. a drug, or an endogenous native compound, in a biological system by enhancing the nuclear polarisation of NMR active nuclei of the test compound (hereinafter termed 'hyperpolarisation') prior to NMR or MRI analysis. The invention also provides a method for carrying out NMR pattern profiling to obtain information on the status of a biological system.

Definitions

The term 'test compound' as used hereinafter, refers to a compound that may be exogenous or endogenous to the biological system in which it is to be studied and that is of physiological interest, e.g. a potential drug substance, which is not a noble gas nor a so-called Overhauser MRI (OMRI) contrast agent or other MR Imaging agent. A test compound must contain at least one NMR active nuclei, i.e. a nuclei with non-zero nuclear spin.

The term 'fate' as used hereinafter when applied to a test compound encompasses metabolism, absorption, distribution and excretion in a biological system.

The term 'biological system' as used hereinafter encompasses whole animals, plants, micro-organisms, isolated organs and tissues, isolated cells or cultured cells isolated sub-cellular organelles and expressed and/or reconstituted enzyme systems. Samples that may be extracted from biological systems such as whole animals, plants, isolated organs or tissues, include tissue or cell samples, faeces, body fluids including but not limited to blood, lymph, urine, semen, breast milk, cerebro-spinal fluid, sweat, lachrymal or parotid secretions or lavage.

Background and Brief Summary of Invention

Due to the genomic revolution, combinatorial chemical libraries and high throughput screening, an exponentially increasing number of new chemical entities is now entering or is already in the trial phases required prior to marketing as new drugs. This rapid evolution of potentially beneficial drugs has led to an increased pressure on both the efficacy and safety evaluation processes. There is an on-going intensive search for new technologies that may optimise the efficiency of such evaluations.

Pharmacokinetic and toxicology testing have two key requirements, which are the identification of metabolites formed from the parent compound and assessment of the toxicity of both the parent compound and its metabolites. During pre-clinical tests and the clinical trial phases of drug development, it is essential to investigate (by detection/monitoring) whether trial drugs themselves or their metabolites give rise to adverse reactions in in vitro test systems, animals, healthy volunteers or patients. It is also necessary to ascertain whether potentially undesirable and even dangerous reactions are related to the concentration or distribution of the drug or one or more of its metabolites in the body. In addition such evaluations may be conducted in selected patients in order to determine whether particular groups of patients with, for instance, identified defects in one or more drug metabolising enzymes (which may represent a very small minority of the pre-clinical and clinical trial populations) are at an increased risk of developing adverse drug reactions. An important aspect of any such investigations is to determine the fate of a drug substance once it has been administered, i.e. its absorption, tissue distribution, rate and site(s) of metabolism, characterisation of structure and relative abundance of metabolites and routes of excretion. There is a need for new methods for studying the fate of a test compound.

One of the methods that can be used to study the fate of a test compound in a biological system is to identify the structures of its metabolites. Current techniques for identifying the structure of metabolites rely heavily on mass spectroscopy (MS) in combination with liquid chromatography. However, mass spectroscopy is, on its own, often not able to characterise the structure of metabolites fully and unambiguously. Data derived from NMR spectroscopy are often complementary to that obtained from MS and when used in combination these techniques may allow the structure of metabolites to be determined. Unfortunately, currently NMR is relatively insensitive. In many cases, the relatively low sensitivity of NMR creates fundamental problems that affect the acquisition time needed in order to achieve a desired signal and the lower limit of detection (LOD) of analyte at a defined signal: noise ratio (e.g. 3:1).

In practical terms, the poor sensitivity of current NMR techniques limits their application in absorption, distribution, metabolism and excretion (ADME) studies. During the early stages of drug development, the supply of candidate drug, and hence its metabolites, is limited and there is often not enough material available for analysis by NMR. In addition, the concentration of metabolites produced by in vitro and in vivo screens is low and often well below the level needed for analysis by NMR. It is not advisable to increase dosing because the routes of metabolism may change under such non-physiological conditions and the metabolites formed will be non-representative of these produced under standard patient treatment regimes.

At present, it is necessary to scale up the testing procedure and to concentrate the metabolites from large volumes of biological fluids (e.g. cell culture superntants, organ perfusates, plasma, bile, urine etc.) in order to characterise the new candidate drugs by NMR. This is very time consuming so, in practice, it often does not take place until late in the drug development phase. This leads to many of the costly late phase candidate drug failures. Ideally, NMR needs to be incorporated as a routine analytical tool alongside MS as early as possible in the evaluation of the ADME characteristics of new chemical entities. However, this is not feasible with the sensitivity of conventional NMR techniques. The present invention using hyperpolarised NMR active nuclei addresses many of the aforementioned limitations and hence offers many advantages compared to conventional NMR techniques, as will be discussed below.

In addition to ADME applications, toxicity (Tox) evaluations are also central to the drug approval process. The current situation with regard to Tox testing is arguably even more problematic than ADME. Many candidate drugs are found to exhibit unacceptable toxicity late in clinical trials, and even occasionally post launch. It is widely accepted within the pharmaceutical industry that current pre-clinical toxicological screens are inadequate. Current in vitro screens are poorly predictive of the in vivo situation. Consequently, the toxicity of new candidate drugs must be evaluated thoroughly in two animal species before large scale testing in humans. This is costly and time consuming. Moreover, results from animal testing are not always predictive for humans. There is an urgent requirement for improved toxicity screening procedures.

Bioanalytical approaches for evaluating drug efficacy and safety currently include measurements of responses of living systems to drug candidates either at the genetic level or at the level of expression of cellular proteins, using so-called genomic and proteomic methods respectively. However, since both methods ignore the dynamic metabolic status of the whole cell, tissue or organism, even in combination genomics and proteomics may not provide sufficient information about integrated cellular function in living systems to assess accurately the fate and toxicological profile of a drug candidate. A high-resolution $^1$H NMR-based approach has been suggested (Xenobiotica, 1999, vol. 29, 1181-1189, J. K. Nicholson et al) and has been termed metabonomics. Metabonomics is defined as the quantitative measurement of the dynamic multiparametric metabolic response of living systems to pathophysiological stimuli or genetic modification. It is anticipated that such analyses will highlight patterns of variations of endogenous compounds produced in response to known toxins. This should enable the toxicity of new candidate drugs to be predicted by comparison. The methods according to the present invention using hyperpolarised NMR should enable improvements in metabonomic analyses of the effect of new candidate drugs on the distribution, metabolism and excretion of endogenous compounds in comparison to currently employed techniques. Hyperpolarised NMR will enable the utilisation of $^{13}$C NMR for these sorts of studies. Currently, only the use of $^1$H NMR is practicable (due to insensitivity of detection for $^{13}$C using conventional NMR) and the information content of the analysis is limited by the chemical shift range of $^1$H. In comparison, $^{13}$C NMR offers a much wider range of chemical shifts. The improvements obtained by the methods of the present invention may be in terms of speed and sensitivity and any combination thereof.

NMR pattern profiling is a technique that is used to acquire information about the status of a biological system (J Pharm Biomed Anal March 1995, 13(3): 205-11, Anthony M L et al; Mol Pharmacol July 1994; 46(1): 199-211, Anthony M L et al; Naturwissenschaften January 1975; 62(1):10-4, Kowalski B R and Bender C F). Typically an NMR pattern, which may be a spectrum or an image, from a system that has been subjected to some kind of perturbation in its state is compared with the NMR pattern from the same type of system in its usual state. Changes in the pattern can then be correlated with the change in state of the system. The change in state of the system may be, for example, exposure to a drug substance, change in environment or a disease, or a change in stage of development of the system. Profiling can be used to compare two systems to determine whether they are in the same or in different states. Once information is available on the pattern exhibited by a type of system in a variety of states, profiling can be used to determine the state of a test system of that type by comparing the pattern exhibited by the test system with the known patterns for that type of system. The information is conveniently stored electronically and algorithmic analyses can be used to compare the pattern for the test system with the known patterns. The algorithmic analyses are suitably carried out using a computer and appropriate software. NMR pattern profiling is potentially a powerful technique for acquiring a plethora of information about a system even when specific entities, for example metabolites, cannot unambiguously be identified individually. However, its usefulness has been limited by the inability of current technology to detect and resolve differences in individual spectra due to the relatively low sensitivity of the NMR technique. The present invention using hyperpolarised NMR active nuclei addresses this limitation and thereby potentially enables NMR pattern profiling to be used to obtain more information than is available using conventional NMR techniques regarding, for example, a system's health, function and metabolic status, and the mechanisms occurring within the system.

The present invention is not limited to any specific method for polarising NMR active nuclei. Such polarisation may be achieved by many different ways, for example, by polarisation transfer from a noble gas, or by one of the 'Brute force' (WO 99/35508, Nycomed Imaging AS), DNP (WO 98/58272, Nycomed Imaging AS) and para hydrogen (p-$H_2$) methods (WO 99/24080, Nycomed Imaging AS) as explained below.

Noble gas isotopes having non-zero nuclear spin can be hyperpolarised, i.e. have their polarisation enhanced over the equilibrium polarisation, e.g. by the use of circularly polarised light. Preferred techniques for hyperpolarisation include spin exchange with an optically pumped alkali metal vapour and metastability exchange. Noble gases to which this technique can be applied include $^3$He and $^{129}$Xe. The enhanced nuclear polarisation of a noble gas can be transferred to another NMR active species in close proximity by spin-spin interaction. WO 97/37239 (Lawrence Berkeley National Laboratory) describes methods for transferring nuclear polarisation from a hyperpolarised noble gas to nuclear spins on a target compound, leading to an enhancement of the corresponding NMR or MRI signals. WO 98/30918 (Nycomed Imaging AS) relates to ex-vivo dynamic nuclear polarisation (DNP) or Nuclear Overhauser Effect (NOE) cross-polarisation from a hyperpolarised gas to an MRI agent where the gas is separated from the MRI agent prior to administration to the body.

Although the NMR spectroscopy or imaging method of the present invention provides similar types of information about the fate of a test compound as conventional NMR or MRI, it offers potential advantages. Among these advantages are: a) increased sensitivity of analysis; and b) increased speed of acquisition of NMR spectra (or images). The analysis of drugs/metabolites or physiological compounds containing an NMR active nuclei may provide additional information previously only supplied by studying corresponding $^{14}$C-labelled compounds, whilst being free from the problems associated with radioactive isotopes.

Furthermore, in comparison to studies using fluorescent reagents and related labelling technology, for example, the current invention does not require the synthesis of an adduct comprising a reporter, e.g. a fluor, and the test compound in order to enable detection. Therefore the present invention offers the following advantages over conventional fluorescence based detection systems:

1. There is no alteration in the chemical structure of novel drugs or physiological compounds. There is always a disadvantage with techniques such as fluorescent methods in that the additional chemical component may influence the measurement. Specifically, the fluorescent label may be of a significant size when compared with the test compound and sometimes as large or larger than the test compound. Consequently the fate of the labelled test compound may be quite different from the non-labelled compound.

2. Fluorescence measurement may not be specific, due for example to dye leakage, dye compartimentalisation, quenching of signal and autofluorescence.

Similarly, although the NMR pattern profiling method of the present invention provides similar types of information about the state of a system when compared to existing NMR pattern profiling methods, it also offers potential advantages. Among those possible advantages are: a) increased sensitivity of analysis; and b) increased speed of acquisition of NMR spectra (or images). Increased detail in pattern profiles, may be realised as a consequence of increased sensitivity such that features become visible within spectra that would not be discernible from noise under conventional NMR. The sensitivity increase enables utilisation of $^{13}C$ NMR as well as $^1H$ NMR which collectively would provide additional information relative to $^1H$ NMR profiles alone. Changes in patterns that are not visible in pattern profiles obtained using conventional NMR techniques may be observed using the method according to the present invention. These small changes may be particularly important for example when studying toxicity or carrying out quality assurance testing on cell cultures.

BRIEF DESCRIPTION OF DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
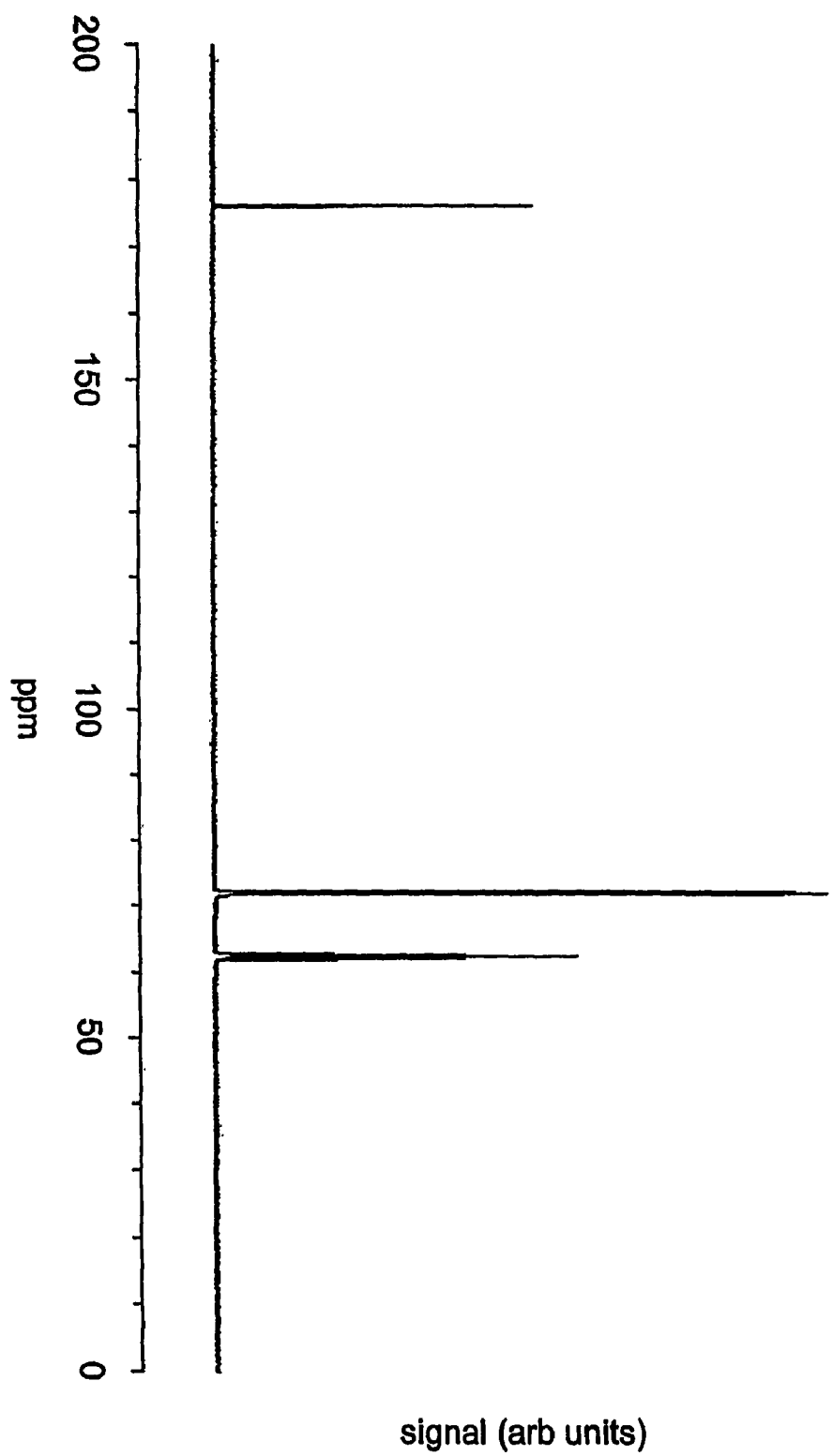
FIG. 1 illustrates the NMR spectrum of (13C carboxyl) Benzoic acid isolated from rat urin wherein the prominent peak from the leaveled $^{13}COOH$ site of benzoic acid is clearly visible at 176.0 ppm and wherein the prominent signals at around 71.9ppm and around 62.3 ppm are identified as solvent peaks from glycerol.

One aspect of the present invention concerns a method for monitoring any aspect of the fate of a test compound, including metabolism, which method comprises polarising one or more NMR active nuclei in the test compound and detecting changes in the spectra of the nuclei. The test compound may be an exogenous compound such as a drug or an endogenous 'native' substance. The changes may be detected continuously or as a series of discrete measurements or as a single measurement. Both quantitative and qualitative measurements are included, especially the dynamic clearance pattern of any metabolites using samples of e.g. exhaled respiratory gases, blood, blood plasma, urine or other body fluids. Suitable nuclei are those with non-zero nuclear spin. Preferred NMR active nuclei are $^{13}C$, $^{15}N$, $^{31}P$, $^{19}F$ and/or $^1H$, $^{13}C$ is particularly preferred Where the test compound is a drug, and isotopic enrichment is appropriate to facilitate detection it is preferred to use stable, non-radioactive isotopes that have substantially no effect on the therapeutic efficacy of the drug, such as $^{13}C$ and $^{15}N$. Alternatively, nuclear species occurring at high natural abundance such as $^{31}P$, $^{19}F$ and/or $^1H$, can be detected according to the methods of the invention.

Where the test compound is exogenous, e.g. a drug, it may be polarised before administration to the system in which its fate is to be studied. Alternatively, for endogenous and exogenous test compounds, the whole system or samples extracted from the system may be subjected to an appropriate hyperpolarisation technique at various times.

Thus, in a first aspect the present invention provides a method for investigating the fate of a test compound containing at least one NMR active nuclei said method comprising:
  administering the test compound to a biological system;
  hyperpolarising the NMR active nuclei in the system-or in a sample extracted from the system; and
  analysing the hyperpolarised system or one or more samples extracted from the system by NMR spectroscopy and/or NMR imaging.

NMR spectroscopy is the preferred method of analysis, particularly where samples extracted from the system are to be analysed.

Suitably, where the system is an animal or perfused organ, samples (e.g. biopsy, necropsy or fluid extract) will be taken and then hyperpolarised. For example, blood or urine samples may be taken. The samples may be purified prior to NMR spectroscopy, but this is not always necessary. An important advantage of the methods according to the present invention is that, unlike with prior art methods, spectroscopy can be carried out directly on the crude biological sample without the need for fractionation, purification or concentration steps.

This method is particularly suitable for dynamic studies as samples may be taken at time intervals, hyperpolarised, and then NMR spectra of the various samples can be compared to show changes over time. Hyperpolarisation may be effected by means of a polarising agent as a single transfer, continuous transfer or intermittent transfer. An appropriate method for hyperpolarisation will be selected depending on the nature of the system or sample.

The test compound is preferably exogenous to the biological system in which its fate is to be studied, e.g. a drug or drug candidate.

In another aspect, the invention provides a method for investigating the fate of a test compound containing at least one NMR active nuclei, which method comprises:
  hyperpolarising the NMR active nuclei in the compound;
  administering the hyperpolarised compound to a biological system; and
  analysing the system or samples extracted from the system by NMR spectroscopy and/or NMR imaging.

An appropriate method of hyperpolarisation will be selected depending on the nature of the test compound.

NMR spectroscopy is the preferred method of analysis, particularly where samples extracted from the system are to be analysed. The test compound is preferably exogenous to the biological system in which its fate is to be studied, e.g. a drug or drug candidate. Again, the samples may be subjected to preliminary steps such as fractionation, purification or concentration prior to spectroscopy, but the fact that this is not always necessary is an advantage of this method.

Suitable NMR active nuclei for use in test compounds for the methods according to the first and second aspects include $^{13}C$, $^{15}N$, $^{31}P$, $^{19}F$ and/or $^1H$. $^{13}C$ and $^{15}N$ are particularly suitable. $^{13}C$ is the most preferred.

Although it may be possible to employ the methods of the invention with test compounds containing a natural abundance of the NMR active nuclei, where the test compound is exogenous, it is preferably enriched with NMR active nuclei before administration to the system. This may include either selective enrichments of one or more sites, or uniform enrichment of all sites. Enrichment can be achieved by chemical synthesis or biological labelling. Preferably, a test compound for use in a method according to the invention is an organic compound comprising an artificially enriched abundance of, for example, $^{13}C$, either generally or at least in one specific position, at an abundance of at least 5%, suitably at least 10%, more suitably at least 50%, preferably at least 75%, more preferably at least 90% and ideally at approaching 100%.

The present invention also covers the use of test compounds comprising an artificially-enriched abundance of $^{15}N$ of at least 1%, suitably at least 5% more suitably at least 10%, preferably at least 50% and more preferably at least 75% or more, and ideally at approaching 100%.

Enrichment of more than one nuclear species, e.g. $^{13}C$ and $^{15}N$ may be performed in the same test compound.

Although it might be expected that, because different $^{13}C$ centres in a uniformly enriched test compound relax at very different rates, very different signal intensities would be found in any NMR spectra produced, surprisingly peaks have been observed even for $^{13}C$ centres that were expected to relax too rapidly to appear in spectra. Thus, a peak for each carbon centre can be observed in spectra produced according to a preferred embodiment of the invention wherein the NMR nuclei are $^{13}C$ and analysis is by spectroscopy.

The degree of hyperpolarisation of the NMR active nuclei or nuclei according to this invention can be measured by its enhancement factor compared to thermal equilibrium at spectrometer field and temperature. Suitably the enhancement factor is at least 10, preferably it is at least 50 and more preferably it is at least 100. However test methods where even smaller enhancements are achieved may still be performed usefully due to the shorter time needed for the total measurement compared with conventional methods. If the enhancement is reproducible and the polarisation/NMR measurement can be repeated, the signal to noise ratio of an NMR signal can be improved. In such a case, the minimum NMR enhancement factor required depends on: a) the polarisation technique and b) the concentration of the test compound. The enhancement has to be large enough so that the NMR signal from the test compound can be detected. In this context, it is clear that an enhancement of 10 or less than 10 that it is achievable in a multi-shot experiment may be very useful due to the time saved in data acquisition compared with conventional NMR.

The analysis steps of the above mentioned methods may be carried out by continuous monitoring or as a single discrete measurement or as a series of discrete measurements that may be carried out at suitable intervals over time. Thus, changes in the spectra or images can be monitored over time and correlated with dynamic events. Such dynamic events may include metabolic events, changes in distribution, progress in absorption, and progress in excretion of the test compound The aforementioned methods may be used to monitor the dynamic fate of any test compound as well as endogenous metabolites or metabolites of exogenous test compound using samples from e.g. blood, urine or other body fluids.

When the fate to be studied relates to metabolism, NMR spectroscopy rather than MRI should be used as the method of analysis. It may be possible, by carrying out the analysis over time, to identify many and preferably all known changes in metabolism or appearance of individual metabolites of the test compound. It should be possible to assign specific peaks in the spectrum to known metabolites. The increased sensitivity of the technique may result in additional peaks (compared with spectra obtained using conventional NMR) due to previously unrecognised minor products of metabolism appearing in the spectrum. This is important because even tiny amounts of toxic metabolites can cause a drug candidate to exhibit damaging side-effects. This method will thus be a very useful tool to evaluate the metabolic/toxicity pattern for a drug or other substances as well as producing mechanistic information.

Metabolic studies can be carried out in whole animals, perfused organs; tissue or cell cultures or in test tube systems utilising, for example, microsomal preparations or other sub cellular fractions such as S9 mix (which contains both phase one and phase two metabolising enzymes). Where whole animals or organs are used, it is preferred to employ the method according to the first aspect of the invention and to hyperpolarise samples extracted from the animal or organ. Blood and urine samples are particularly suitable. Studying urine samples has the advantage of enabling cumulative effects to be observed.

The methods will be particularly useful when some of the metabolites are not previously known. The chemical shift from the polarised NMR active nuclei may help to identify the nature of the new metabolites.

In addition, the methods may also be useful even if it is not possible to identify the different metabolites unequivocally because in some situations the dynamic clearance pattern from unknown metabolites may also have a significant value.

When the fate of the test compound to be studied is absorption, the system is conveniently a whole animal, perfused organ, tissue or cell system. Whole animals and perfused organs, especially whole animals, are particularly suitable. Typically, samples are extracted from different locations in the system and analysed by NMR spectroscopy. Alternatively, the whole system can be analysed by NMR imaging. In one embodiment, the test compound is hyperpolarised and then administered to the human or animal body by inhalation. Absorption of the test compound via the lungs is monitored by NMR imaging. In another embodiment, the test compound is hyperpolarised, then administered to the human or animal body by intravenous injection and absorption from the bloodstream is observed by NMR imaging.

If it is desired to investigate the distribution of a test compound, it is preferred to hyperpolarise the compound and then administer it to a whole animal or human body. The compound may be administered by inhalation, or alternatively it can be administered intravenously. NMR imaging is preferably used to monitor the distribution of the test compound. Suitably, imaging can be carried out continuously. Alternatively, a series of discrete images can be produced over time. NMR imaging can be carried out on the whole human or animal body. Alternatively, solid sections can be taken from an animal that has been killed at a known time interval from administration of the test compound and these sections can be imaged. In this case, the solid sections are hyperpolarised before imaging.

If the fate of the test compound to be investigated is excretion, it is preferred to administer the test compound to a whole animal and then to extract samples of, for example, bile, saliva, faeces, urine or exhaled air. These samples are hyperpolarised prior to NMR analysis. NMR spectroscopy should be employed in studies of this type.

In a third aspect, the present invention provides a method for investigating the state of a biological system containing at least one NMR active nuclei, which method comprises:
    hyperpolarising the NMR active nuclei; and
    analysing the system or samples extracted from the system by NMR spectroscopy and/or NMR aging to generate a NMR pattern of the system.

The hyperpolarisation step may be carried out on the whole system or on a sample extracted from the system.

In one preferred embodiment, the following additional steps are carried out:

subjecting the system to a change in its state;
hyperpolarising the NMR nuclei;
analysing the system or samples extracted from the system in its changed state by NMR spectroscopy and/or NMR imaging to generate an NMR pattern of the system in its changed state;
comparing the NMR patterns of the system and the system in its changed state and identifying any changes in the NMR pattern.

The changes in NMR patterns identified in the final step can be correlated with the change in state of the system.

Alternatively, two or more systems of the same type may be studied. The first, or test, system is subjected to a change in its state, while the second, or control system is not. The hyperpolarisation and analysis steps are carried out on each system and the NMR patterns are compared and any differences between patterns for the test system and the control system are identified.

Thus, in the fourth aspect, the present invention provides a method for investigating the state of a biological system containing at lease one NMR active nuclei which comprises:

subjecting the system to a change in its state;
hyperpolarising the NMR nuclei;
analysing the system or samples extracted from the system by NMR spectroscopy or NMR imaging to generate an NMR pattern of the test system;
comparing the pattern with a pattern obtained from a control system that was not subjected to a change in its state prior to hyperpolarisation and analysis; and
identifying any differences between the pattern from the test system and the pattern from the control system.

Several test systems can be subjected to the same or different changes in state and their NMR patterns can be compared with the pattern from a single control system.

The state of the system may be changed by external or internal influences. Examples of external influences include exposure to an exogenous substance, such as a drug or other type of test compound, or alterations in the environment of the system, e.g. changes in temperature or pH. An example of an internal influence is the development of the system over time, e.g. cell growth and differentiation.

Suitably the NMR patterns are stored electronically, for example in a database. Algorithmic analysis is conveniently used to carry out the comparison step, typically by employing a computer with appropriate software.

NMR spectroscopy is the preferred method of analysis. The NMR active nuclei is suitably a nuclei with non-zero nuclear spin. Preferred active nuclei are $^{13}C$, $^{15}N$, $^{31}P$, $^{19}F$ and/or $^{1}H$. $^{13}C$ is particularly preferred.

The methods can be repeated to acquire NMR patterns for a system in a number of different states. This information is conveniently stored electronically, for example in a database. When one or more NMR patterns are available for a system in a known state or states, these can be compared with the NMR pattern for a system of the same type in an unknown state. If the NMR patterns are substantially similar or the same for the system in a known state and the system in an unknown state, the unknown state will be the same or similar to the known state. Normally, the more NMR patterns available for a particular type of system in a variety of states, the more likely it is to find a pattern substantially similar or the same as the pattern for a test system of that type in an unknown state.

Thus, in a fifth aspect, the invention provides a method for investigating the state of a test biological system containing at least one NMR active nuclei, which method comprises:

hyperpolarising the NMR active nuclei;
analysing the test system or samples extracted from the test system by NMR spectroscopy and/or NMR imaging to generate an NMR pattern for the test system;
comparing the NMR pattern for the test system with the NMR pattern for at least one other system of the same type as the test system, said other system being in a known state when its pattern was generated;
determining the state of the test system.

The hyperpolarisation step may be-carried out on the system or on a sample extracted from the system.

Conveniently, the comparison step is carried out by algorithmic analysis, for example by using a computer with suitable software. Suitably, the NMR pattern for the test system is compared with several other NMR patterns and preferably with a significant number of other NMR patterns stored electronically, for example in a database.

The accuracy of this method will depend, amongst other factors, on the similarity of the test system with the systems of the same type for which NMR patterns are available. Thus, more accurate results will be obtained regarding the state of isolated test cells where the cells are derived from the same lineage, tissue and species as the cell cultures for which patterns are known, than if the test cells are derived from a different cell lineage, tissue or species. The method is particularly useful for quality assurance testing of systems that are intended to be the same, e.g. cell cultures, wherein small but physiologically significant differences can be detected.

The methods of the third, fourth and fifth aspects are useful for investigating responses of a biological system to a compound, e.g. a drug, about which relatively little is known. Useful data about the effects of the compound can be obtained by comparing the NMR pattern of a system exposed to it in various quantities with the NMR patterns for the system when exposed to other compounds. For example, the patterns observed for cells derived from human liver when exposed to a test compound can be compared with NMR patterns for the same cells when exposed to substances with known effects on the liver. If the pattern for cells exposed to the test compound is similar to the pattern for cells exposed to a compound that is known to have liver toxicity, it is likely that the test compound will also exhibitliver toxicity. This is particularly useful when a baseline of pre and post testing strategies can be established using the same system. NMR profiling can also provide important structural information about unknown compounds.

The profiling methods of the third, fourth and fifth aspects are particularly suitable for studying plants.

A polarised noble gas, preferably $^{3}He$ or $^{129}Xe$, or a mixture of such gases, may be used according to the present invention to effect nuclear polarisation of the test compound or system comprising at least one NMR active nuclei. The hyperpolarisation may also be achieved by using an artificially enriched hyperpolarised noble gas, preferably $^{3}He$ or $^{129}Xe$. The hyperpolarised gas may be in the gas phase, it may be dissolved in a liquid, or the liquefied hyperpolarised gas itself may serve as a solvent. Alternatively, the gas may be condensed onto a cooled solid surface and used in this form, or allowed to sublime. Either of these methods may allow the necessary intimate mixing of the polarised gas with the target to occur. In some cases, liposomes or microbubbles may encapsulate the hyperpolarised noble gas.

In a further embodiment, the present invention provides a method wherein the polarisation may be imparted to atoms of significance in the test compound or system (e.g. $^{13}$C, $^{15}$N, $^{31}$P, $^{29}$Si, $^{19}$F and $^{1}$H isotopes) by thermodynamic equilibration at a very low temperature and high field. Hyperpolarisation compared to the operating field and temperature of the NMR spectrometer is effected by use of a very high field and very low temperature (Brute force). The magnetic field strength used should be as high as possible, suitably higher than 1T, preferably higher than 5T, more preferably 15T or more and especially preferably 20T or more. The temperature should be very low e.g. 4.2K or less, preferably 1.5K or less, more preferably 1.0K or less, especially preferably 100 mK or less. It will be appreciated that this embodiment is not suitable for polarising a viable biological system where that system is a whole animal, isolated organ or tissue or cultured cells.

In a further embodiment, the present invention provides a method for polarisation transfer using the DNP method effected by a DNP agent, to effect nuclear polarisation of the test compound or system comprising at least one NMR active nuclei. DNP mechanisms include the Overhauser effect, the so-called solid effect and the thermal mixing effect.

Most known paramagnetic compounds may be used as a "DNP agent" in this embodiment of the invention, e.g. transition metals such as chromium (V) ions, magnesium (II) ions, organic free radicals such as nitroxide radicals and trityl radicals (WO 98/58272) or other particles having associated free electrons. Where the DNP agent is a paramagnetic free radical, the radical may be conveniently prepared in situ from a stable radical precursor by a radical-generating step shortly before the polarisation, or alternatively by the use of ionising radiation. During the DNP process, energy, normally in the form of microwave radiation, is provided, which will initially excite the paramagnetic species. Upon decay to the ground state, there is a transfer of polarisation to a NMR active nuclei of the target material. The method may utilise a moderate or high magnetic field and very low temperature, e.g. by carrying out the DNP process in liquid helium and a magnetic field of about 1T or above. Alternatively, a moderate magnetic field and any temperature at which sufficient NMR enhancement is achieved in order to enable the desired studies to be carried out may be employed. The method may be carried out by using a first magnet for providing the polarising magnetic field and a second magnet for providing the primary field for MR spectroscopy/imaging. It will be appreciated that, as in the Brute force method described above, that this embodiment is not suitable for polarising a viable biological system where that system is a whole animal, isolated organ, or tissue or cultured cells if high fields and low temperatures are used.

It might be expected that the presence of a paramagnetic radical would cause line-broadening and susceptibility shifts in NMR spectra produced in analysing the sample. Pleasingly, this does not occur in the experiments carried out to date. This good result may be explained by the low relaxivity of the radical used and its low concentration in the final sample. Therefore it is preferred to use a DNP radical with low relaxitivity in those embodiments of the invention where a DNP radical is required.

In a further embodiment, the present invention provides a para hydrogen induced polarisation method. Hydrogen molecules exist in two different forms, para hydrogen (p-H$_2$) where the nuclear spins are anti parallel and out of phase (singlet state) and ortho hydrogen (0-H$_2$) where the spins are parallel or anti parallel and in phase (triplet state). At room temperature, the two forms exist in equilibrium with a 1:3 ratio of para:ortho hydrogen. However, preparation of para hydrogen enriched hydrogen can be carried out a low temperature, 160K or less, in the presence of a catalyst. The para hydrogen formed may be stored for long periods, preferably at low temperature, e.g. 18-20K. Alternatively it may be stored in pressurised gas form in containers which have an inner surface which is non-magnetic and non-paramagnetic.

The preparation of a para hydrogen-containing species is achieved by exposing an unsaturated precursor (containing NMR active nuclei) of the compound to the para hydrogen-enriched hydrogen gas in the presence of a suitable catalyst. This enriched hydrogen will then react with the precursor by reduction imparting a non-thermodynamic spin configuration to the target molecule. The compounds suitable for use are thus prepared from precursors which can be reduced by hydrogenation and which will therefore typically possess one or more unsaturated bonds, e.g. double or triple carbon-carbon bonds.

When the p-H$_2$ molecule is transferred to the precursors of the compound (by means of catalytic hydrogenation with e.g. (PPh$_2$)$_3$RhCl), the proton spins remain anti parallel and begin to relax to thermal equilibrium with the normal constant T1 of the hydrogen in the compound. However, during relaxation some of the polarisation may be transferred to neighbouring nuclei by pulse sequence Progress in Nuclear Spectroscopy, 31, (1997), 293-315), low field cycling or other types of coupling. The presence of the NMR active nuclei as e.g. $^{13}$C (and $^{15}$N etc) with a suitable substitution pattern close to the relaxing hydrogen may lead to the polarisation being trapped in the slowly relaxing $^{13}$C (and $^{15}$N etc) resulting in a high enhancement factor.

This embodiment is suitable for the aspects of the invention in which the NMR active nuclei in the test compound is hyperpolarised prior to administration to the system in which its fate is to be tested.

A further hyperpolarisation transfer embodiment of this invention is the spin refrigeration method. This method covers spin polarisation of a solid compound or system by spin refrigeration polarisation. The system is doped with or intimately mixed with a suitable paramagnetic material such as Ni$^{2+}$, lanthanide and actinide ions in crystal form with a symmetry axis of order three or more. The instrumentation is simpler than that required for DNP, with no need for a uniform magnetic field since no resonant excitation field is applied. The process is carried out by physically rotating the sample around an axis perpendicular to the direction of the magnetic field. The pre-requisite for this method is that the paramagnetic species has a highly anisotropic g-factor. As a result of the sample rotation, the electron paramagnetic resonance will be brought in contact with the nuclear spins, leading to a decrease in the nuclear spin temperature. Sample rotation is carried out until the nuclear spin polarisation has reached a new equilibrium. Again, it will be appreciated that this embodiment is not suitable for polarising a biological system where that system is a whole animal, isolated organ or tissue or cultured cells.

When a test compound, system or sample from a system has been hyperpolarised, it is desirable to preserve as much as possible of the polarisation prior to NMR analysis. Some of the hyperpolarisation techniques described above are only effective when transferring polarisation in the solid state. However, it is often desired to investigate the NMR spectrum of a compound sample or system in the liquid state, in order to improve spectral resolution and sensitivity. Alternatively, line-narrowing techniques such as Magic Angle Spinning (MAS) can be employed to increase spectral resolution of NMR in the solid state and enable low temperature NMR analysis.

If the compound, sample or system is not solid, it may conveniently be frozen in an appropriate solvent mixture prior to polarisation transfer by one of the methods that needs to be carried out in the solid state. Solvent mixtures have been found to be particularly suitable, especially if the mix forms an amorphous glass. The amorphous matrix is employed to ensure homogenous intimate mixing of radical and target in the solid while the sample is subject to DNP polarisation.

If a liquid state NMR technique is to be employed, once the compound, sample or system has been hyperpolarised, it can be rapidly removed from the polarisation chamber and then dissolved in a suitable solvent. It is advantageous to use solvents that will not interfere with the images or, more usually, the spectra produced in the analysis step. Deuterated solvents such as $D_2O$ are particularly suitable. Stirring, bubbling, sonification or other known techniques can be used to improve the speed of dissolution. Suitably, the temperature and pH of the solution are maintained to allow optimal dissolution and a long nuclear relaxation time.

Preferably, the compound, sample or system and then the solution thereof are kept in a holding field throughout the period between polalrisation and analysis in order to prevent relaxation. A holding field provides a field higher than the Earth's magnetic field and suitably higher than 10 mT. It is suitably uniform in the region of the sample. Although a holding field is not required for all test compounds, much better results are obtained for some test compounds when such a field is used and it is difficult to predict in advance which compounds will require such a holding field, especially if the structure of the compound is not known a priori. Therefore, it is preferable to use a holding field whenever a system or sample is polarised and then transferred for analysis. The optimal conditions will depend on the nature of the compound, sample or system. The solution is subsequently transferred for examination by standard solution phase NMR analysis. The transfer process is preferably automated. Alternatively, the polarisation transfer and dissolution steps are suitably integrated into a single automated unit. In an additional suitable embodiment, the polarisation transfer and sample dissolution steps are automated and NMR detection hardware is also housed within the same single fully integrated unit. A holding field will not be required with such a fully integrated system.

Different $^{13}C$ centres relax at very different rates. Consequently, very different signal intensities would be expected to appear in the resulting NMR spectra if nuclear relaxation occurs during the transfer from the hyperpolarisation unit to the NMR spectrometer. Surprisingly, peak heights from different centres within uniformly $^{13}C$ enriched molecules have been observed to be of the same order. A possible explanation is that the effect may be due to a redistribution of the enhanced polarisation by cross-relaxation at certain carbon centres. This is useful, because it allows more information to be obtained than may otherwise have been expected. It is not unreasonable to assume that any carbon centre within a given test compound will be detected with similar sensitivity.

Alternatively, where a solid state NMR technique is to be used, the solid state compound, sample or system may be hyperpolarised, e.g. by DNP, brute force, spin refrigeration transfer or any other method that will work in the solid state at low temperature. Subsequently, the hyperpolarised sample will be moved into a solid-state MAS NMR probe. The movement is suitably rapid and is conveniently carried out via lifting or ejection. The sample in the NMR probe will then be spun so that high-resolution solid state NMR spectroscopy can be carried out. The entire process can be automated and will preferably be carried out in an integrated unit.

The invention will now be illustrated by reference to the following non-limiting examples.

EXAMPLES

Trityl Radical

Stable triarylmethyl reagents are particularly suitable for DNP enhancements. The radical used in the following examples is tris (8-carboxyl-2,2,6,6,-tetra(2(1-hydroxyethyl))benzo[1,2-d:4,5-d']bis(1,3)dithiol-4-yl)methyl sodium salt (hereafter called trityl radical). This was made according to the methods described in WO98/39277.

Stock solutions of trityl radical were prepared in deuterated glycerol for each example.

To glycerol-$D_8$ (200 µl) was added trityl radical (6.28 mg). The radical was dissolved by stirring under gentle heating and brief sonication and was stored in a closed vial until required. This yielded a stock at 22 mM which was used in the study of benzoic acid (example 1); the final trityl radical concentration used for the DNP step was 13.2 mM. Samples of trityl radical solution were gently warmed to facilitate subsequent dispensing. Similarly a stock of trityl radical was prepared at 22.25 mM and this was employed for the hippuric acid in urine sample (example 4) with a final radical concentration of 14.9 mM for the DNP step. Additionally a stock was prepared at 25 mM and this was used for the remaining studies (examples 2,3,5 and 6), with final radical concentrations of 15 mM for the DNP steps.

40% $^W$/v Sodium deutoxide was purchased from SIGMA/ALDRICH chemical company and was diluted 100 fold in $D_2O$ to prepare a 0.4% $^W$/v. stock which was used in examples 1,2 and 3.

Glycerol-$D_8$, $D_2O$ and DMSO-$D_6$ reagents were purchased from SIGMA/ALDRICH

Example 1

Study of ($^{13}C$-carboxyl) Benzoic Acid Isolated From Rat Urine.

($^{13}C$-carboxyl) Benzoic acid was purchased from SIGMA/Aldrich chemical company. A sample was added to rat urine at approximately 5 mg per ml and then isolated by solid phase extraction (SPE) and reversed phase high performance liquid chromatography (RP hplc, C18 Kromasil, 25×1 cm, 5 µm) using gradient elution with formic acid in water and formic acid in methanol. The isolated material was then dried and an aliquot re-analysed by RP hplc indicating a purity of 94%, with the main component co-eluting with carrier material, monitored by on-line UV detection (at 254 nm) and yielding the expected (M—H)⁻ ion at 122 mass units by on-line electrospray ionisation mass spectrometry (EI-MS).

A sample of ($^{13}C$-carboxyl) benzoic acid (89 µg, 0.72 µmol) obtained as described above was dissolved in sodium deutoxide in $D_2O$ (0.4% $^W$/v, 7.5 ul, approximately 1.5 equivalents) and $D_2O$ (7.5 µl). Trityl radical dissolved in glycerol-$D_8$ (24 µl, 22 mM) was added to the benzoic acid solution and the subsequent cocktail was mixed to homogeneity with a disposable plastic pipette. The sample was rapidly frozen, as small droplets, by dripping via a fine plastic pipette into a liquid nitrogen bath. The frozen sample drops were collected using small tweezers and placed in a liquid nitrogen cooled Kel-F cup and this was transferred for sample polarisation. The sample was polarised overnight at a magnetic field of 3.354T and at a microwave frequency of 93.925 GHz. Microwave power was 100 mW and sample temperature was maintained at 1.25K for the duration of polarisation. The test sample was dissolved in hot $D_2O$ (approximately 5 ml) in situ and a portion (approximately 1 ml in a 5 mm NMR tube, estimated sample temperature is 333K) was rapidly transferred to an INOVA 400 MHz spectrometer for measurement of a liquid state NMR spectrum. The sample was exposed to the earth's magnetic field during transit to the spectrometer (approximately 20 seconds transfer time). The signal to noise estimated for the carboxyl carbon of ($^{13}$C-carboxyl) benzoic acid peak, observed at 176.0 ppm is approximately 440. The NMR spectrum was obtained in a single acquisition (acquisition time was 1.2 seconds, sweep width 25 kHz, following a RF pulse of 6 microseconds, with WALTZ proton de-coupling applied during the pulse and acquisition; line broadening of 1 Hz was applied and signal to noise was determined by Varian Vnmr software). The same sample was subsequently analysed by non enhanced NMR with proton decoupling in the same spectrometer. A thermal equilibrium signal for the carbonyl carbon was obtained with a signal to noise of approximately 8. This control spectrum was acquired in 37 hours (averaging 168000 scans with a scan repetition rate of 0.8 seconds and a flip angle of 11.2 degrees i.e. under Ernst angle conditions.

The sample used for NMR analysis was retained and subsequently re-analysed by RP hplc (C18 Kromasil, 25×0.46 cm, 5 µm) with gradient elution with formic acid in water and formic acid in acetonitrile and by EI-MS).

Re-analysis indicated predominantly ($^{13}$C) benzoic acid and the material yielded the expected molecular ion by MS analysis.

Results

The spectrum of FIG. 1 was obtained. The prominent peak from the labelled $^{13}$COOH site of benzoic acid is clearly visible at 176.0 ppm. The prominent signals at around 71.9 ppm and around 62.3 ppm are identified as solvent peaks from glycerol. The acquisition time for this spectrum was a matter of seconds, compared to the days that would be required by conventional NMR. The spectrum illustrates an exceptional signal to noise ratio.

Conclusions

The observed signal to noise ratio of the enhanced NMR spectrum, compared with the signal to noise ratio of the conventional NMR spectrum from the same sample, confirms that the method according to the invention gives substantial improvement. The enhancement is estimated to be of the order of a few thousandfold. Similarly, the remarkably short data acquisition time is evidence that the methods of the invention may be used to carry out studies that would simply be too time-consuming to do in practice using conventional NMR.

The lines of the spectrum are very narrow and are positioned as expected in the spectrum. Therefore, it can be inferred that the DNP radical is not affecting the quality of the NMR spectrum. This is important because it shows that the signal enhancement obtained by using this hyperpolarisation method of the invention is not compromised by artefacts in the enhanced spectrum obtained.

Example 2

Study of ($^{13}$C-carboxyl) Hippuric Acid (Primary Benzoic Acid Metabolite) Isolated from Rat Urine After iv Administration of ($^{13}$C-carboxyl) Benzoic Acid.

Embodiment Without a Holding Field Magnet ($^{13}$C-carboxyl) Benzoic acid was administered intravenously at 10 mg/Kg (at 0 and 2 hrs) to 4 anaesthetised rats; urine was collected from canulated urethra. The major metabolite ($^{13}$C-carboxy) hippuric acid was isolated by SPE and RP-hplc. The isolated material was then dried and an aliquot re-analysed by RP hplc indicating a purity of 99%, with the main component co-eluting with authentic carrier material, monitored by on-line UV detection (at 254 nm) and yielding the expected (M−H)$^-$ion at 179 mass units by on-line electrospray ionisation mass spectrometry (EI-MS).

A sample of ($^{13}$C-carboxyl) hippuric acid (463 µg, 2.57 µmol) obtained as described above was dissolved in sodium deutoxide in D$_2$O (0.4% $^W$/v, 17.5 µl, approximately 0.97 equivalents). Trityl radical dissolved in glycerol-D$_8$ (26 µl, 25 mM) was added to the hippuric acid solution and the subsequent cocktail was mixed to homogeneity with a disposable plastic pipette. The sample was rapidly frozen, as small droplets, by dripping via a fine plastic pipette into a liquid nitrogen bath. The frozen sample drops were collected using small tweezers and placed in a liquid nitrogen cooled Kel-F cup and this was transferred for sample polarisation. The sample was polarised for 4 hours at a magnetic field of 3.354T and at a microwave frequency of 93.925 GHz. Microwave power was 100 mW and sample temperature was maintained at 1.25K for the duration of polarisation. The test sample was dissolved in hot D$_2$O (2-3 ml) in situ and a portion (approximately 1 ml in a 5 mm NMR tube, estimated sample temperature is 333K) was rapidly transferred to an INOVA 400 MHz spectrometer for measurement of a liquid state NMR spectrum.

Results

The NMR spectrum was obtained in a single acquisition (acquisition time was 1.2 seconds, sweep width 25 kHz, following a RF pulse of 6 microseconds; $^1$H decoupling was employed as above; line broadening of 1 Hz was applied and signal to noise was determined by Varian Vnmr software). A very noisy NMR spectrum from Hippuric acid was obtained. The signal to noise estimated for the carboxyl carbon peak of ($^{13}$C-carboxyl) hippuric acid, observed at approximately 170 ppm is less than 4. Strong glycerol signals were observed.

Results

Example 3

Study of ($^{13}$C-carboxyl) Hippuric Acid (Benzoic Acid Metabolite) Isolated from Rat Urine After iv Administration of ($^{13}$C-carboxyl Benzoic Acid.

Embodiment Utilising a Holding Magnet

A sample of ($^{13}$C-carboxyl) hippuric acid (463 µg, 2.57 µmol) obtained as described above was dissolved sodium deutoxide in D$_2$O (0.4% $^W$/v, 17.5 µl, approximately 0.97 equivalents). Trityl radical dissolved in glycerol D$_8$ (26 µl, 25 mM) was added to the hippuric acid solution and the subsequent cocktail was mixed to homogeneity with a disposable plastic pipette. The sample was rapidly frozen, as small droplets, by dripping via a fine plastic pipette into a liquid nitrogen bath. The frozen sample drops were collected using small tweezers and placed in a liquid nitrogen cooled Kel-F cup and this was transferred for sample polarisation. The sample was polarised for 4 hours at a magnetic field of 3.354T and at a microwave frequency of 93.925 GHz. Microwave power was 100 mW and sample temperature was maintained at 1.25K for the duration of polarisation. The test sample was dissolved in hot D$_2$O (2-3 ml) in situ and a portion (approximately 1 ml in a 5 mm NMR tube, estimated sample temperature is 333K) was rapidly transferred to an INOVA 400 MHz spectrometer for measurement of a liquid state $^{13}$C NMR spectrum. The sample was maintained in a magnetic holding field of 10 mT during transit to the spectrometer (approximately 20 seconds transfer time). The signal to noise estimated for the carboxyl carbon of ($^{13}$C-carboxyl) hippuric acid peak, observed at 171.2 ppm, is approximately 1500. An NMR spectrum was obtained in a single acquisition (acquisition time was 1.2 seconds, sweep width 25 kHz, following a RF pulse of 6 microseconds; $^1$H decoupling was employed as above line broadening of 1 Hz was applied and signal to noise was determined by Varian Vnmr software).

The sample used for NMR analysis was retained and subsequently re-analysed by RP hplc (C18 Kromasil, 25×0.46 cm, 5 µm) with gradient elution with formic acid in water and formic acid in acetonitrile and by EI-MS). Re-analysis indicated predominantly ($^{13}$C) hippuric acid and the material yielded the expected molecular ion by MS analysis.

Results

Figure 2:
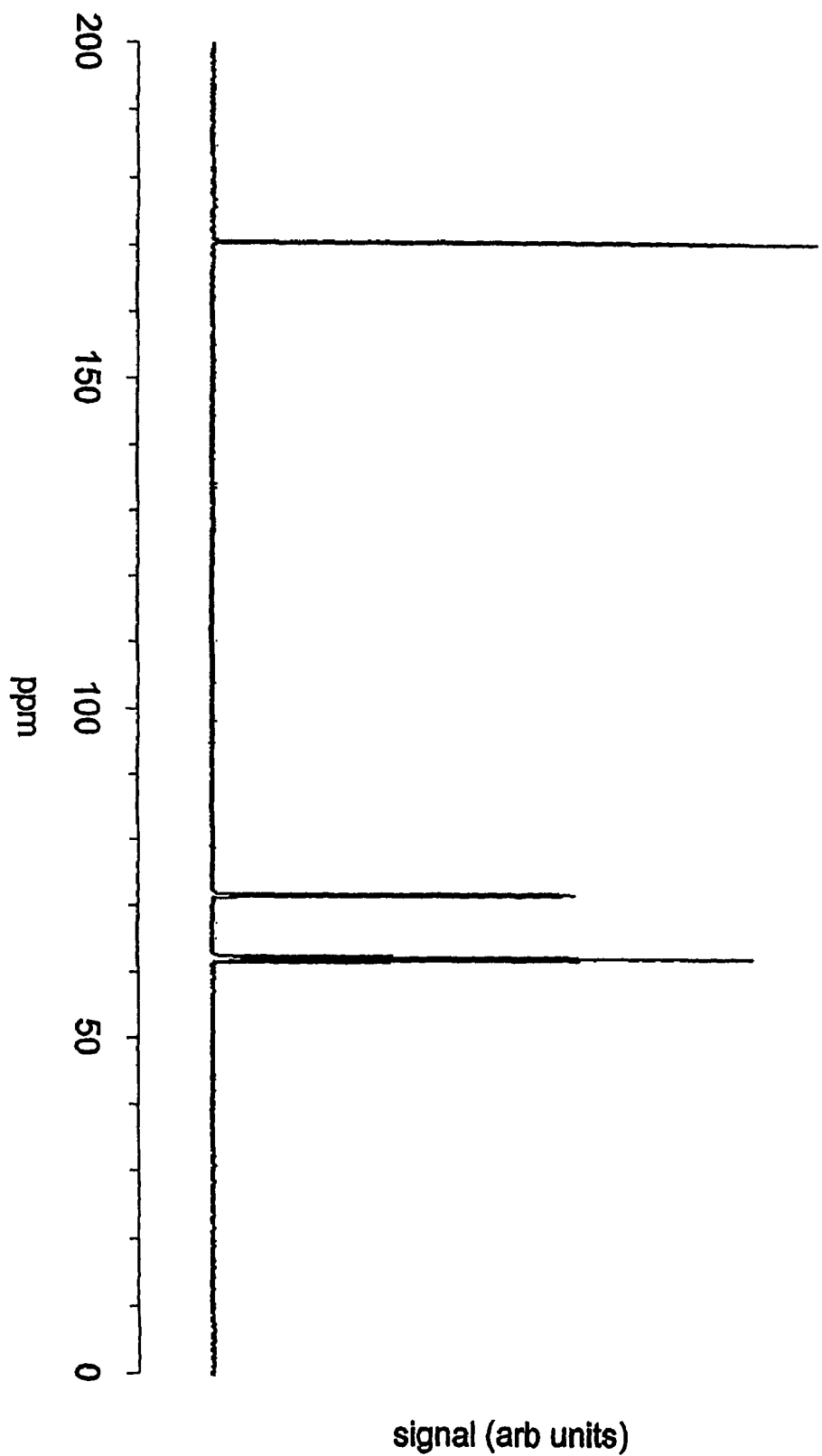
FIG. 2 illustrates an enhanced NMR spectrum of a sample isolated from rat uring after administration of (13C-carboxyl) Benzoic acid.

The enhanced NMR spectrum is shown in FIG. 2. A much higher signal to noise ratio for the hippuric acid NMR signal was obtained in this example using a holding field than in Example 2 where no holding field was used.

Pleasingly, peaks in addition to that expected for the label were observed.

The chemical shift difference of the NMR signal from the hippuric acid label compared to that from the benzoic acid label was as expected from conventional NMR studies.

Conclusions

It is beneficial to use a holding field when analysing some compounds by a technique where the sample is polarised in one location and NMR analysis takes place in another. Since it is not always possible to predict in advance which compounds will benefit from the use of such a holding field, it should be used routinely when ex situ hyperpolarisation techniques are employed.

The presence of additional peaks from the hippuric acid in the enhanced NMR spectrum indicates that the methods of the invention are suitable for studying test compounds at lower doses than would be possible using the conventional NMR. This is potentially significant for studying toxicity and or metabolism of drugs and drug candidates, where some metabolites may be present only at very low concentrations.

Moreover, it can be inferred from the presence of additional peaks that the methods of the invention may be suitable for use with test compounds wherein there is a lower degree of enrichment or even natural abundance of the NMR active nuclei.

The observation of NMR signals at the expected chemical shift positions confirms that this method of the invention does not introduce artefacts and can be used to study the fate of the test compound.

Example 4

($^{13}$C-carboxyl) Hippuric Acid (Analysed Directly After Spiking into Rat Urine)

($^{13}$C-carboxyl) Hippuric acid was synthesised in-house from ($^{13}$C-carboxyl) benzoic acid and glycine.

A sample was added to rat urine at approximately 5 mg/ml, which was the level measured in urine (0-2 hr collection) in the benzoic acid metabolism study described above. A sample containing 95 µg of synthetic ($^{13}$C-carboxyl) hippuric acid was dissolved in approximately 20 µl of rat urine. Trityl radical dissolved in glycerol-$D_8$ (30 ul, 22.25 mM) was added to the hippuric acid solution and the subsequent cocktail was mixed to homogeneity with a disposable plastic pipette. The sample was rapidly frozen, as small droplets, by dripping via a fine plastic pipette into a liquid nitrogen bath. The frozen sample drops were collected using small tweezers and placed in a liquid nitrogen cooled Kel-F cup and this was transferred for sample polarisation. The sample was polarised for 4 hours at a magnetic field of 3.354T and at a microwave frequency of 93.925 GHz. Microwave power was 100 mW and sample temperature was maintained at 1.25K for the duration of polarisation. The test sample was dissolved in hot $D_2O$ (2-3 ml) in situ and a portion (approximately 1 ml in a 5 mm NMR tube, estimated sample temperature is 333K) was rapidly transferred to an INOVA 400 MHz spectrometer for measurement of a liquid state $^{13}$C NMR spectrum. The sample was maintained in a magnetic holding field of 10 mT during transit to the spectrometer (approximately 20 seconds transfer time).

The signal to noise estimated for the carboxyl carbon of ($^{13}$C-carboxyl) hippuric acid peak, observed at 171.1 ppm, is approximately 534. An NMR spectrum was obtained in a single acquisition (acquisition time was 1.2 seconds, sweep width 25 kHz, following a RF pulse of 6 microseconds $^1$H decoupling was employed as above; line broadening of 1 Hz was applied and signal to noise was determined by Varan Vnmr software).

The sample used for NMR analysis was retained and subsequently re-analysed by RP hplc (C18 Kromasil, 25×0.46 cm, 5 um) with gradient elution with formic acid in water and formic acid in acetonitrile and by EI-MS). Re-analysis indicated predominantly ($^{13}$C) hippuric acid and the material yielded the expected molecular ion by MS analysis.

Results

Two NMR signals were observed, one arising from hippuric acid at 170.7 ppm and one smaller singlet NMR signal at 163.1 ppm that can be assigned tentatively to urea, because its chemical shift is consistent with the shift predicted using ACD Labs software, and this substance is known to be a major constituent of urine.

Conclusions

In this case, a test compound was analysed directly in a biological matrix, i.e. rat urine. The fact that a clear signal was obtained is very encouraging and confirms that samples collected over time could be analysed, thus enabling dynamic studies. Another conclusion is that samples may not need to be fractionated prior to NMR analysis.

It is not unreasonable to infer that had benzoic acid also been present in the sample, it would also have been detected. Accordingly, pharmacokinetic studies could be undertaken using the methods of the invention.

Example 5

(U-$^{13}$C)Paracetamol Isolated from Rat Urine (U-$^{13}$C)Paracetamol was synthesised. This material was added to rat urine at approximately 5 mg per ml and then isolated by solid phase extraction (SPE) and reversed phase high performance liquid chromatography (RP hplc, C18 Kromasil, 25×1 cm, 5 µm) using gradient elution with formic acid in water and formic acid in methanol.

The isolated material was then dried and an aliquot reanalysed by RP hplc indicating a purity of 94%, with the main component co-eluting with carrier material monitored by on-line UV detection (at 254 nm) and yielding the expected (M+H)$^+$ ion at 160 mass units by on-line electrospray ionisation mass spectrometry (EI-MS).

A sample of (U-$^{13}$C) paracetamol (312 µg, 1.96 µmol) obtained as described above was dissolved in DMSO-$D_6$ (10 µl) and $D_2O$ (14 µl). Trityl radical dissolved in glycerol-$D_8$ (36 µl, 25 mM) was added to the (U-$^{13}$C) paracetamol solution and the subsequent cocktail was mixed to homogeneity with a disposable plastic pipette. The sample was rapidly frozen, as small droplets, by dripping via a fine plastic pipette into a liquid nitrogen bath. The frozen sample drops were collected using small tweezers and placed in a liquid nitrogen cooled Kel-F cup and this was transferred for sample polarisation. The sample was polarised for 4 hours at a magnetic field of 3.354T and at a microwave frequency of 93.925 GHz. Microwave power was 100 mW and sample temperature was maintained at 1.25K for the duration of polarisation. The test sample was dissolved in hot $D_2O$ (2-3 ml) in situ and a portion (approximately 1 ml in a 5 mm NMR tube, estimated sample temperature is 333K) was rapidly transferred to an INOVA 400 MHz spectrometer for measurement of a liquid state $^{13}C$ NMR spectrum. The sample was maintained in a magnetic holding field of 10 mT during transit to the spectrometer (approximately 20 seconds transfer time). An NMR spectrum was acquired in a single acquisition (acquisition time was 1.2 seconds, $^1H$ discoupling was employed as above, sweep width 25 kHz, following a RF pulse of 6 microseconds).

The sample used for NMR analysis was retained and subsequently re-analysed by RP hplc (C18 Kromasil, 25×0.46 cm, 5 um) with gradient elution with formic acid in water and formic acid in acetonitrile and by EI-MS). Re-analysis indicated predominantly ($^{13}C$) paracetamol and the material yielded the expected molecular ion by MS analysis.

Results

An enhancement was observed with all peaks being present at positions consistent with prediction.

Example 6

Study of (U-$^{13}C$)paracetamol-sulphate Isolated from Rat Bile After iv Administration of (U-$^{13}C$)paracetamol (U-$^{13}C$)Paracetamol was administered intravenously at 20 mg/kg (at 0 and 3 hrs) to 4 anaesthetised rats, urine was collected from canulated urethra and bile was collected from canulated bile duct (2 rats only) at 0-3 and 3-6 hours. Bile (3-6 hrs) was extracted with dichloromethane and then fractionated by RP-hplc (C18 Kromasil, 25×1 cm, 5 um) using gradient elution with formic acid in water and formic acid in methanol).

Several metabolites were collected. Paracetamol sulphate was identified by on-line EI-MS, from its (M+H)$^+$ ion at 240 mass units. The isolated material was then dried and an aliquot re-analysed by RP hplc indicating a peak purity of 96.7%, monitored by on-line UV detection (at 254 nm) and gave the expected (M+H)+ ion at 240 mass units by on-line electrospray ionisation mass spectrometry (EI-MS).

A sample of (U-$^{13}C$) paracetamol-sulphate (100 g, 0.42 μmol) obtained as described above was dissolved in $D_2O$ (24 μl). Trityl radical dissolved in glycerol-$D_8$ (36 μl, 25 mM) was added to the (U-$^{13}C$) paracetamol solution and the subsequent cocktail was mixed to homogeneity with a disposable plastic pipette. The sample was rapidly frozen, as small droplets, by dripping via a fine plastic pipette into a liquid nitrogen bath. The frozen sample drops were collected using small tweezers and placed in a liquid nitrogen cooled Kel-F cup and this was transferred for sample polarisation. The sample was polarised for 4 hours at a magnetic field of 3.354T and at a microwave frequency of 93.925 GHz. Microwave power was 100 mW and sample temperature was maintained at 1.25K for the duration of polarisation. The test sample was dissolved in hot $D_2O$ (2-3 ml) in situ and a portion (approximately 1 ml in a 5 mm NMR tube, estimated sample temperature is 333K) was rapidly transferred to an INOVA 400 MHz spectrometer for measurement of a liquid state $^{13}C$ NMR spectrum. The sample was maintained in a magnetic holding field of 10 mT during transit to the spectrometer (approximately 20 seconds transfer time). An NMR spectrum was acquired in a single acquisition (acquisition time was 1.2 seconds, sweep width 25 kHz, following a RF pulse of 6 microseconds $^1H$ decoupling was applied as above).

The sample used for NMR was retained and subsequently re-analysed by RP hplc (C18 Kromasil, 25×0.46 cm, 5 μm) with gradient elution with formic acid in water and formic acid in acetonitrile and by EI-MS). Re-analysis indicated a major component with a retention time consistent with paracetamol sulphate from previous analysis and the material yielded the expected molecular ion by MS analysis.

Results

Figure 3:
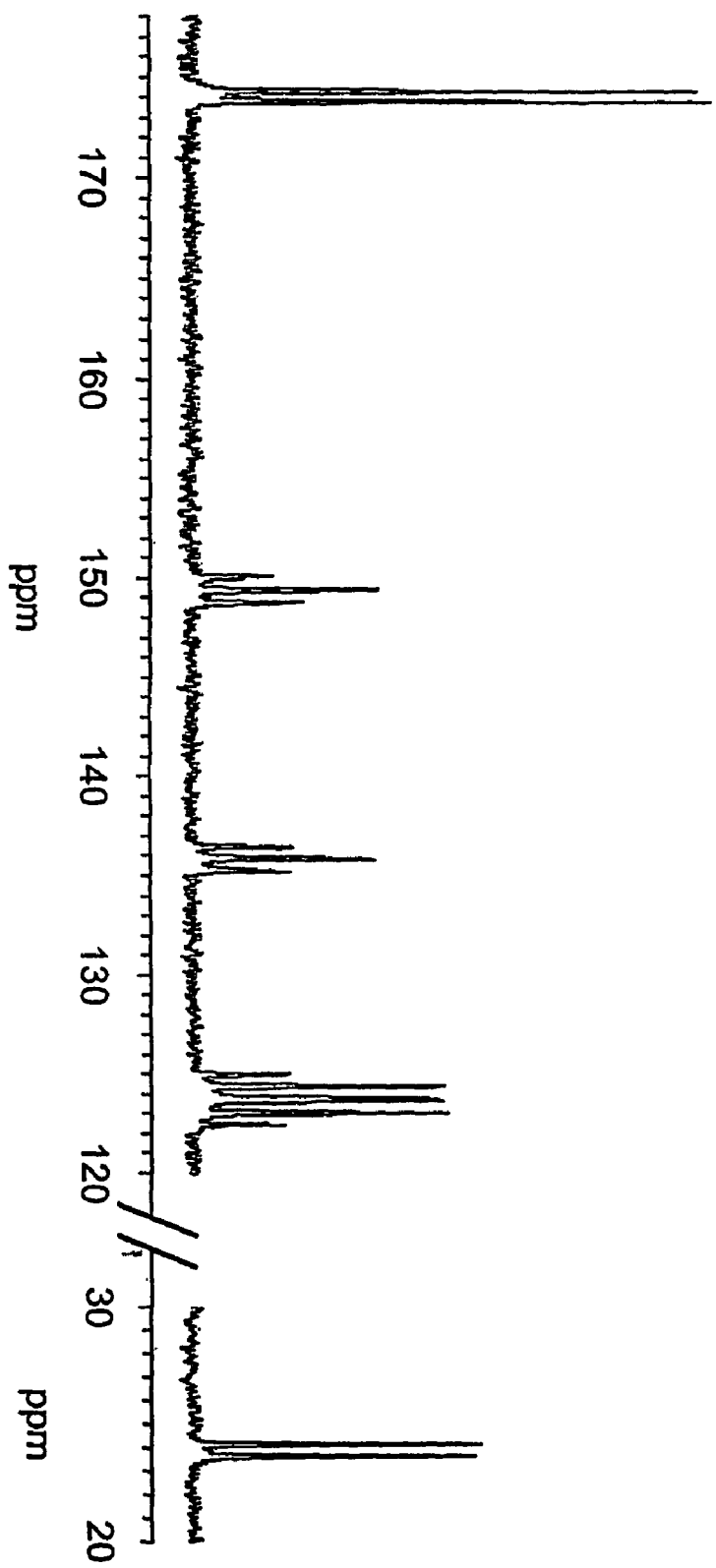
FIG. 3 illustrates an enhanced NMR spectrum of a sample isolated from rate bile after administration of (U-13C) paracetamol.

The enhanced NMR spectrum is shown in FIG. 3. Differences were observed in the spectrum for paracetamol sulphate compared with paracetamol. In particular, the chemical shift positions for $^{13}C$ NMR signals arising from aromatic sites are significantly different.

The peak heights for the carbon centres were of the same order.

Conclusions

The paracetamol sulphate had been produced by metabolism in a rat and was collected from bile. Bile is a different biological matrix than urine (from which the hippuric acid and benzoic acid were collected. The results indicate that NMR enhancements can be observed irrespective of the biological matrix from which the test compound is derived. The fact that a different spectrum was obtained compared with paracetamol confirms that it may be possible to differentiate between peaks from parent compounds and their metabolites in a mixture, even in the case of subtle structural differences between them.

A pleasing observation was that, as in all the other examples, no signals arising from the radical, were observed.

It was surprising to see that the peak heights for the carbon centres were of the same order. Since different carbon centres decay at very different rates, it was expected that the signal intensities for the carbon centres would be very different. Indeed, it was not expected to be possible to observe the methyl peaks at all. Therefore, more information was obtained from the experiment than anticipated. It is not unreasonable to assume that any carbon centre within a given test compound would be detected with similar sensitivity by the method of the invention.

What is claimed is:

1. A method for investigating the fate of a test compound, said method comprising the steps of:
    administering the test compound to a biological system in which the fate of the test compound is to be studied, wherein the test compound is enriched with $^{13}C$;
    extracting samples from the system over time;
    hyperpolarising the NMR active nuclei in the samples extracted from the system over time, wherein said hyperpolarising is carried out by polarization transfer using solid state dynamic nuclear polarization (DNP) effected by a DNP agent;
    subjecting the samples to a treatment resulting in solid to liquid phase transition; and
    analysing each of said samples by NMR spectroscopy in the liquid state.

2. A method according to claim 1, wherein the hyperpolarised sample is retained in a holding field in the period from hyperpolarisation to analysis.

3. A method according to claim 1, wherein the metabolism of a test compound is studied.

4. A method according to claim 1, wherein the system is one of a whole animal and a human body.

5. A method according to claim 1 for studying absorption of a test compound wherein the system is one of a whole animal and a human body.

* * * * *